(12) United States Patent
Nicolosi et al.

(10) Patent No.: US 7,972,062 B2
(45) Date of Patent: Jul. 5, 2011

(54) OPTICAL POSITIONER DESIGN IN X-RAY ANALYZER FOR COAXIAL MICRO-VIEWING AND ANALYSIS

(75) Inventors: Joseph A. Nicolosi, Alford, MA (US); Robert Westerdale, Hewitt, NJ (US); Bruce Elliott Scruggs, Doylestown, PA (US); Sun Park, Paramus, NJ (US)

(73) Assignee: EDAX, Inc., Mahwah, NJ (US)

( * ) Notice: Subject to any disclaimer, the term of this patent is extended or adjusted under 35 U.S.C. 154(b) by 165 days.

(21) Appl. No.: 12/503,878

(22) Filed: Jul. 16, 2009

(65) Prior Publication Data

US 2011/0013744 A1 Jan. 20, 2011

(51) Int. Cl.
*A61B 6/08* (2006.01)
(52) U.S. Cl. ............... 378/205; 378/44; 378/62; 378/70
(58) Field of Classification Search ............... 378/43, 378/44, 62, 63, 70–90, 205
See application file for complete search history.

(56) References Cited

U.S. PATENT DOCUMENTS

| | | |
|---|---|---|
| 3,889,113 A | 6/1975 | Rhodes |
| 3,919,548 A | 11/1975 | Porter |
| 3,925,660 A | 12/1975 | Albert |
| 3,983,397 A | 9/1976 | Albert |
| 4,048,496 A | 9/1977 | Albert |
| 5,249,216 A | 9/1993 | Ohsugi et al. |
| 5,365,563 A | 11/1994 | Kira et al. |
| 5,408,512 A | 4/1995 | Kuwabara et al. |
| 5,732,120 A | 3/1998 | Shoji et al. |
| 5,740,223 A | 4/1998 | Ozawa et al. |
| 5,912,939 A | 6/1999 | Hirsch |
| 5,937,026 A | 8/1999 | Satoh |
| 5,946,089 A | 8/1999 | Duer |
| 5,978,442 A | 11/1999 | Kuwabara |
| 6,028,911 A | 2/2000 | Kawahara |
| 6,041,095 A | 3/2000 | Yokhin |
| 6,052,431 A | 4/2000 | Onoguchi et al. |

(Continued)

FOREIGN PATENT DOCUMENTS

DE 102005028904 A1 1/2007

OTHER PUBLICATIONS

T. Hara et al. "Revolver undulator for BL15XU at SPring-8", Nuclear Instruments and Methods in Physics Research, 2001, pp. 161-164.

*Primary Examiner* — Jurie Yun
(74) *Attorney, Agent, or Firm* — The Webb Law Firm

(57) ABSTRACT

An X-ray analyzer includes a sample stage for holding and positioning a sample and an optical positioner assembly configured above the sample stage. The optical positioner assembly includes a body member having an opening; an optical positioner located within the opening; and at least one X-ray optic and an optical viewing lens coupled to a first camera. The at least one X-ray optic and the optical viewing lens are secured to the optical positioner. The optical positioner is configured to align one of the at least one X-ray optic and the optic viewing lens normal to the sample on the sample stage such that the sample is irradiated with X-rays through the X-ray optic along a path which is normal to the sample and coaxial with the optic viewing lens receiving light reflected from the sample when the optic viewing lens is positioned normal to the sample.

39 Claims, 5 Drawing Sheets

U.S. PATENT DOCUMENTS

| | | |
|---|---|---|
| 6,108,398 A | 8/2000 | Mazor et al. |
| 6,233,307 B1 | 5/2001 | Golenhofen |
| 6,240,159 B1 | 5/2001 | Kohno et al. |
| 6,292,532 B1 | 9/2001 | Kawahara et al. |
| 6,310,935 B1 | 10/2001 | Kuwabara |
| 6,324,251 B1 | 11/2001 | Kuwabara |
| 6,345,086 B1 | 2/2002 | Ferrandino et al. |
| 6,389,102 B2 | 5/2002 | Mazor et al. |
| 6,477,226 B1 | 11/2002 | Lehmann et al. |
| 6,487,269 B2 | 11/2002 | Anderson |
| 6,700,951 B2 | 3/2004 | Sumii |
| 6,801,595 B2 | 10/2004 | Grodzins et al. |
| 6,882,701 B2 | 4/2005 | Ferrandino et al. |
| 6,885,726 B2 | 4/2005 | Uehara et al. |
| 6,907,108 B2 | 6/2005 | Yokhin et al. |
| 6,925,148 B2 | 8/2005 | Shiota et al. |
| 6,965,663 B2 | 11/2005 | Ohzawa |
| 7,023,954 B2 | 4/2006 | Rafaeli et al. |
| 7,187,751 B2 | 3/2007 | Kawahara et al. |
| 7,245,696 B2 | 7/2007 | Yun et al. |
| 7,258,485 B2 | 8/2007 | Nakano et al. |
| 7,298,817 B2 | 11/2007 | Chen et al. |
| 2001/0021240 A1 | 9/2001 | Kojima et al. |
| 2002/0054661 A1 | 5/2002 | Anderson |
| 2002/0172322 A1 | 11/2002 | Kawahara et al. |
| 2002/0186812 A1 | 12/2002 | Sumii |
| 2003/0133536 A1 | 7/2003 | Kuwabara et al. |
| 2003/0142781 A1 | 7/2003 | Kawahara et al. |
| 2004/0096029 A1 | 5/2004 | Shiota et al. |
| 2006/0088139 A1 | 4/2006 | Nakano et al. |
| 2006/0280285 A1 | 12/2006 | Terada |
| 2007/0003012 A1 | 1/2007 | Taguchi et al. |
| 2007/0030956 A1 | 2/2007 | Hornig |
| 2007/0086567 A1 | 4/2007 | Kataoka et al. |

OPTICAL POSITIONER DESIGN IN X-RAY ANALYZER FOR COAXIAL MICRO-VIEWING AND ANALYSIS

BACKGROUND OF THE INVENTION

1. Field of the Invention

The present invention, in general, relates to an X-ray and optical analyzing device and, more particularly, to a microscopic X-ray and optical analyzing device for performing material analysis having coaxial viewing and analysis.

2. Description of Related Art

Typically, microscopic X-ray analyzing devices combine an optical microscope with a micro-beam X-ray analyzer for non-destructive sample analysis. This combination allows for elemental imaging analysis such as studying compositional homogeneity of samples. To create an elemental image, a sample is analyzed multiple times, typically as a matrix of points. The individual spectra are incorporated into a database and elemental images are created with pixels calculated based on some property such as X-ray intensity or weight percent. Each image pixel is related to the parent spectrum and a position on the sample.

Prior art microscopic X-ray analyzers position the X-ray beam within an incident angular range of $45° \leq \theta \leq 70°$ to the sample and the camera normal to the sample. However, the positioning of the X-ray beam at such an angle introduces some difficulties in the analysis of a sample. For instance, positioning the sample at a precise distance from the X-ray optic is important so that the incident X-ray beam impinges on the sample at the calibrated position within the sample video field of view. Also, the positioning of an X-ray beam at such an angle produces an elliptical spot, complicating the specification of the beam spot size for the analyst. On the other hand, an X-ray spot will have a simpler circular shape achieving the absolute minimum spot size allowable by the X-ray optic in all directions from the center of the X-ray spot if the X-ray beam is positioned normal (i.e., perpendicular) to the sample.

One solution to the problems of such prior art analyzers is disclosed in U.S. Pat. No. 6,965,663 to Ohzawa. This analyzer irradiates a sample with X-rays narrowed down by an X-ray guide member from above the sample. A mirror is provided to allow an optical image of the sample to be obtained in a direction coaxial with the X-ray guide member. However, this configuration also suffers from various deficiencies. For instance, the mirror used to allow for coaxial imaging of the sample limits the design of the X-ray optics or the number of X-ray optics immediately available to the user. Another problem with such a design is that the use of such a mirror may limit the optical image quality or field of view of the sample.

Another possible design for an analyzer is disclosed in U.S. Pat. No. 6,345,086 to Ferrandino et al. This system includes an X-ray source, X-ray focusing element, and a tapered X-ray opaque focusing aperture that provides a focused X-ray spot on a sample. The system translates a sample between an imaging position and a testing position. In the imaging position, the sample is aligned in three dimensions and, after alignment, the system automatically translates the sample between the imaging position and the testing position. To avoid collision between the sample and other components of the system, a position detecting device terminates the sample translation if the sample trips the position detecting device. Accordingly, this system automatically translates the sample between an imaging position and a testing position. However, the movement of a sample in such a manner may cause a loosely mounted sample to shift while the stage is transitioning between the viewing and analyzing positions.

Accordingly, a need exists for a microscopic X-ray analyzer that allows for coaxial viewing and analyzing of a sample. A further need exists for a microscopic X-ray analyzer that allows for multiple X-ray optics to quickly and easily be placed normal to the sample for analysis without moving the sample.

SUMMARY OF THE INVENTION

The present invention provides a method and apparatus that allows for coaxial microscopic viewing and X-ray analyzing of a sample that overcomes the deficiencies of the prior art analyzers. In addition, the present invention provides a microscopic X-ray analyzer that allows for multiple X-ray optics to quickly and easily be placed normal to the sample for analysis without moving the sample.

The present invention is directed to an X-ray analyzer which includes a sample stage for holding and positioning a sample and an optical positioner assembly configured above the sample stage. The optical positioner assembly includes a body member having an opening; an optical positioner, such as a rotary turret or x-y stage, positioned within the opening; and at least one X-ray optic and an optic viewing lens coupled to a first camera. The at least one X-ray optic and the optic viewing lens are secured to the optical positioner. The X-ray analyzer also includes at least one X-ray tube optically coupled to the at least one X-ray optic, and at least one X-ray detector positioned to view the sample through a port of the body member of the optical positioner assembly. The optical positioner is configured to align the optic viewing lens normal to the sample on the sample stage such that the optic lens receives light reflected from the sample along a first path when the optic viewing lens is positioned normal to the sample and to position one of the at least one X-ray optic such that the sample is irradiated with X-rays along a second path when the X-ray optic is positioned normal to the sample.

The first path and the second path may be substantially coaxial. The optical positioner assembly may include a plurality of X-ray optics, such as three, secured to the optical positioner. Each of the plurality of X-ray optics may provide an X-ray beam to the sample having a different spot size, excitation conditions, or beam geometry.

The X-ray analyzer may include more than one X-ray detector, each of which may be suitable for a particular spectral collection characteristic. For example, such particular spectral collection characteristics may be: X-ray energy resolved for X-ray fluorescence spectroscopy, X-ray characteristic line intensity resolved for quantitative and Compton/Rayleigh ratio analysis, and directionally resolved for X-ray diffraction. By these spectral analysis methods, elemental information is determined by the energy of X-ray fluorescent lines, elemental concentrations are determined by characteristic line intensities, average atomic mass (density) is determined by the intensity ratio of Compton to Rayleigh energies, and interatomic d-spacings are determined by the spatial distribution of scattered radiation.

The X-ray analyzer may also include more than one X-ray tube, each of which may be optimized for excitation conditions or for a particular type of X-ray analysis: fluorescence, transmission, Compton, or diffraction.

The X-ray analyzer may further include a second camera positioned to view the sample through a port provided in the body member of the optical positioner assembly. The first camera may be a high-resolution camera and the second camera may be a low-resolution camera. The optical positioner may be positioned by a motive force. The motive force may be provided by a piezoelectric motor or any other suitable motor. The optical positioner may include an optical encoder to provide accuracy in positioning one of the at least one X-ray optic and the optic viewing lens normal to the sample on the sample stage. The optical positioner assembly may further include at least one laser extending through the body for proper positioning of the sample stage.

The present invention is also directed to an optical positioner assembly for use with an X-ray analyzer. The optical positioner assembly includes a body member having an opening; an optical positioner such as a rotary turret or x-y stage positioned within the opening; and at least one X-ray optic and an optic viewing lens coupled to a first camera. The optical positioner is configured to align the optic viewing lens normal to a sample and one of the at least one X-ray optic.

The optical positioner assembly may include a plurality of X-ray optics, such as three, secured to the optical positioner. Each of the plurality of X-ray optics may provide an X-ray beam to the sample having a different spot size, excitation conditions, or beam geometry.

The present invention is also a method of analyzing a sample. The method includes the steps of providing an X-ray analyzer that includes a sample stage for holding and positioning a sample and an optical positioner assembly positioned above the sample stage. The optical positioner assembly includes a body member having an opening; an optical positioner positioned within the opening; an optical viewing lens coupled to a camera; and at least one X-ray optic. The optical viewing lens and the at least one X-ray optic are secured to the optical positioner. The X-ray analyzer also includes at least one X-ray tube optically coupled to the at least one X-ray optic, and at least one X-ray detector positioned to view a sample through a port of the body member of the optical positioner assembly. The method further includes placing a sample on the sample stage; aligning the optical positioner until the optical viewing lens is positioned normal to the sample; imaging a portion of the sample using the camera by receiving light reflected from the sample along a first path to obtain an image of the sample; and locating a point, points, or areas for analysis. The method may further includes the step of aligning the optical positioner until the at least one X-ray optic is positioned along a second path normal to the sample and irradiating the sample with X-rays along a second path. Finally, the method may include the step of detecting an X-ray spectrum from the sample with the at least one X-ray detector along a third path.

The X-ray spectrum provides elemental and atomic structure information of the sample. For example, X-ray energy resolved for fluorescence, X-ray characteristic line intensity resolved for quantitative and Compton/Rayleigh ratio analysis, and directionally resolved for X-ray diffraction. By these spectral analysis methods: elemental information is determined by the energy of X-ray fluorescent lines, elemental concentrations are determined by characteristic line intensities, average atomic mass (density) is determined by the intensity ratio of Compton to Rayleigh energies, X-ray absorption information is obtained from X-rays transmitted through a sample, and interatomic d-spacings are determined by the spatial distribution of scattered radiation.

Optimum excitation conditions for one or more of these X-ray analyses may be achieved by selecting one or more specific X-ray optics. The physical characteristics of a sample are determined from one or more of these X-ray analyses. By sequentially collecting multiple X-ray spectra from a selected area on the sample, maps of elements, concentrations, absorption, atomic mass, and d-spacing are obtained. An overlay of the optical view (video image) of the sample obtained along a first path may be correlated with pixels of element, atomic mass, or d-spacing in maps obtained by X-ray analyses from a second path on the sample.

The method of analyzing samples may include the use of more than one X-ray tube, each of which may be optimized for excitation conditions or for a particular type of X-ray analysis, for example, elemental analysis by X-ray fluorescence spectroscopy, X-ray absorption by transmission, interatomic d-spacing analysis by X-ray diffraction, or atomic mass analysis by analysis of Compton scattering in the X-ray spectra.

The method of analyzing samples may also include more than one X-ray detector, each of which may be suitable for a particular spectral collection characteristic, for example, energy resolved for X-ray fluorescence and Compton, X-ray intensity resolved for quantitative and absorption analyses, and spatially resolved for X-ray diffraction.

The X-ray optics in the optical positioner may be replaced by one or more optics for Infrared (IR) to Ultraviolet (UV) spectroscopy and Raman Spectroscopy. For example, IR spectroscopy exploits the fact that molecules have specific frequencies at which they rotate or vibrate corresponding to discrete energy levels (vibrational modes). These resonant frequencies are determined by the shape of the molecular potential energy surfaces, the masses of the atoms, and the associated vibronic coupling. The infrared portion of the electromagnetic spectrum is divided into three regions; the near-, mid-, and far-IR, named for their relation to the visible spectrum. The far-infrared, approximately 400-10 $cm^{-1}$ (1000-30 $\mu m$) has low energy and may be used for rotational spectroscopy. The mid-IR, approximately 4000-400 $cm^{-1}$ (30-2.5 $\mu m$) may be used to study the fundamental vibrations and associated rotational-vibrational structure. The higher energy near-IR, approximately 14000-4000 $cm^{-1}$ (2.5-0.8 $\mu m$) can excite overtone or harmonic vibrations.

Ultraviolet-Visible spectroscopy (UV-Vis) or ultraviolet-visible spectrophotometry (UV/Vis) involves the spectroscopy of photons in the UV-visible region. The absorption in the visible ranges directly affects the color of the chemicals involved. In this region of the electromagnetic spectrum, molecules undergo electronic transitions. This optical absorption technique is complementary to optical fluorescence spectroscopy, in that fluorescence deals with transitions from the excited state to the ground state, while absorption measures transitions from the ground state to the excited state (see Skoog, et al. *Principles of Instrumental Analysis.* 6th ed. Thomson Brooks/Cole. 2007, 169-173.). UV-Vis spectroscopy is routinely used in the quantitative determination of solutions of transition metal ions and highly conjugated organic compounds. Raman spectroscopy is a spectroscopic technique used in condensed matter physics and chemistry to study vibrational, rotational, and other low-frequency modes in a system. It relies on inelastic scattering, or Raman scattering, of monochromatic light, usually from a laser in the visible, near infrared, or near ultraviolet range. The laser light interacts with phonons or other excitations in the system, resulting in the energy of the laser photons being shifted up or down. The shift in energy gives information about the phonon modes in the system. Infrared spectroscopy yields similar, but complementary, information. Collectively, these optical UV-Vis and Raman Spectroscopy methods are hereinafter referred to as Optical Spectroscopy.

Two or more paths for X-ray analysis, as well as the paths for Optical Spectrometry, may be substantially coaxial. Additionally, Optical Spectrometers may be mounted through one of the ports in the body member of the optical positioner assembly.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. As used in the specification and the claims, the singular form of "a", "an", and "the" include plural referents unless the context clearly dictates otherwise.

DETAILED DESCRIPTION OF THE PRESENT INVENTION

Figure 1:
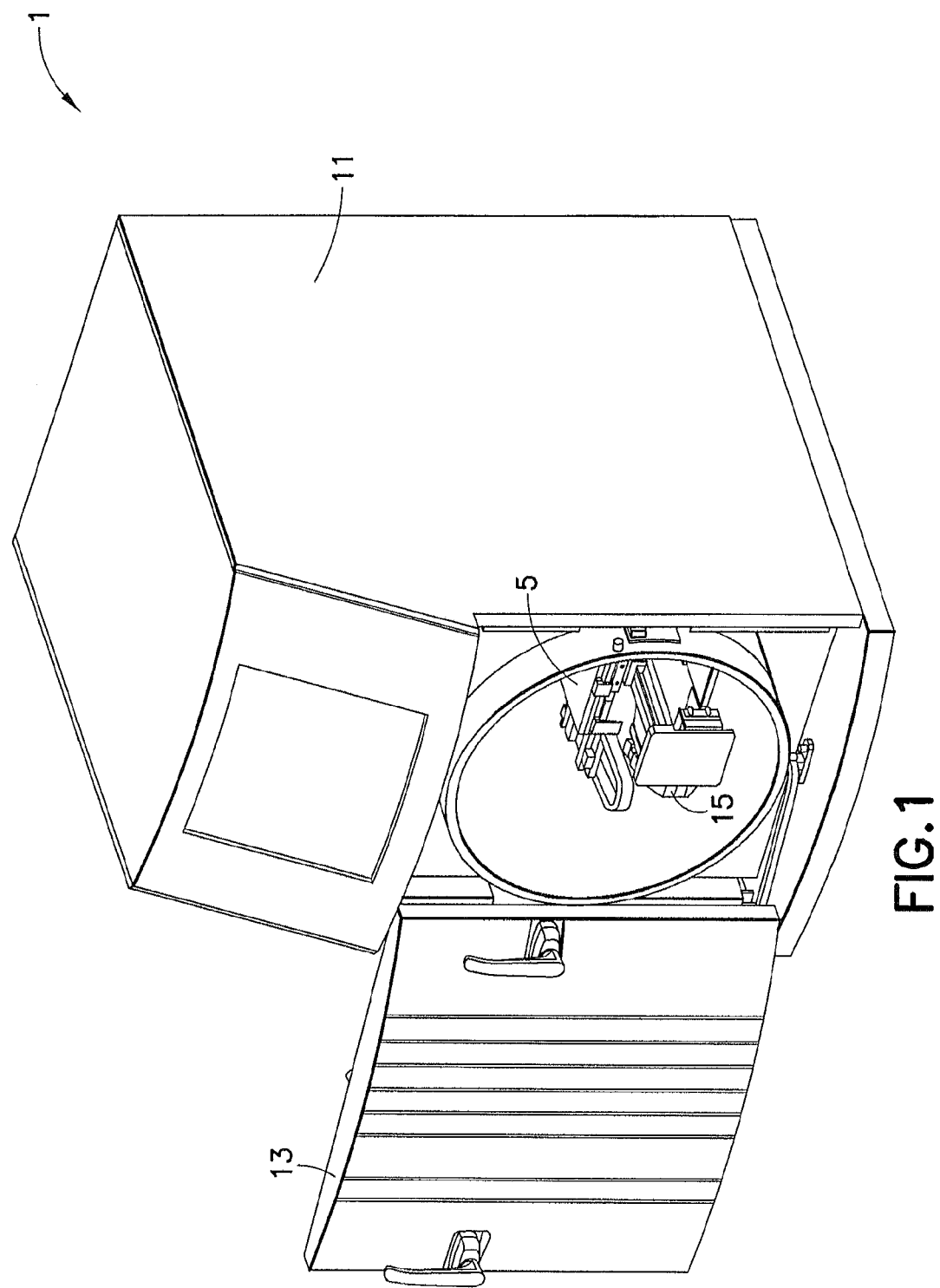
FIG. 1 is a perspective view of an X-ray analyzer in accordance with the present invention positioned within a housing.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Figure 2:
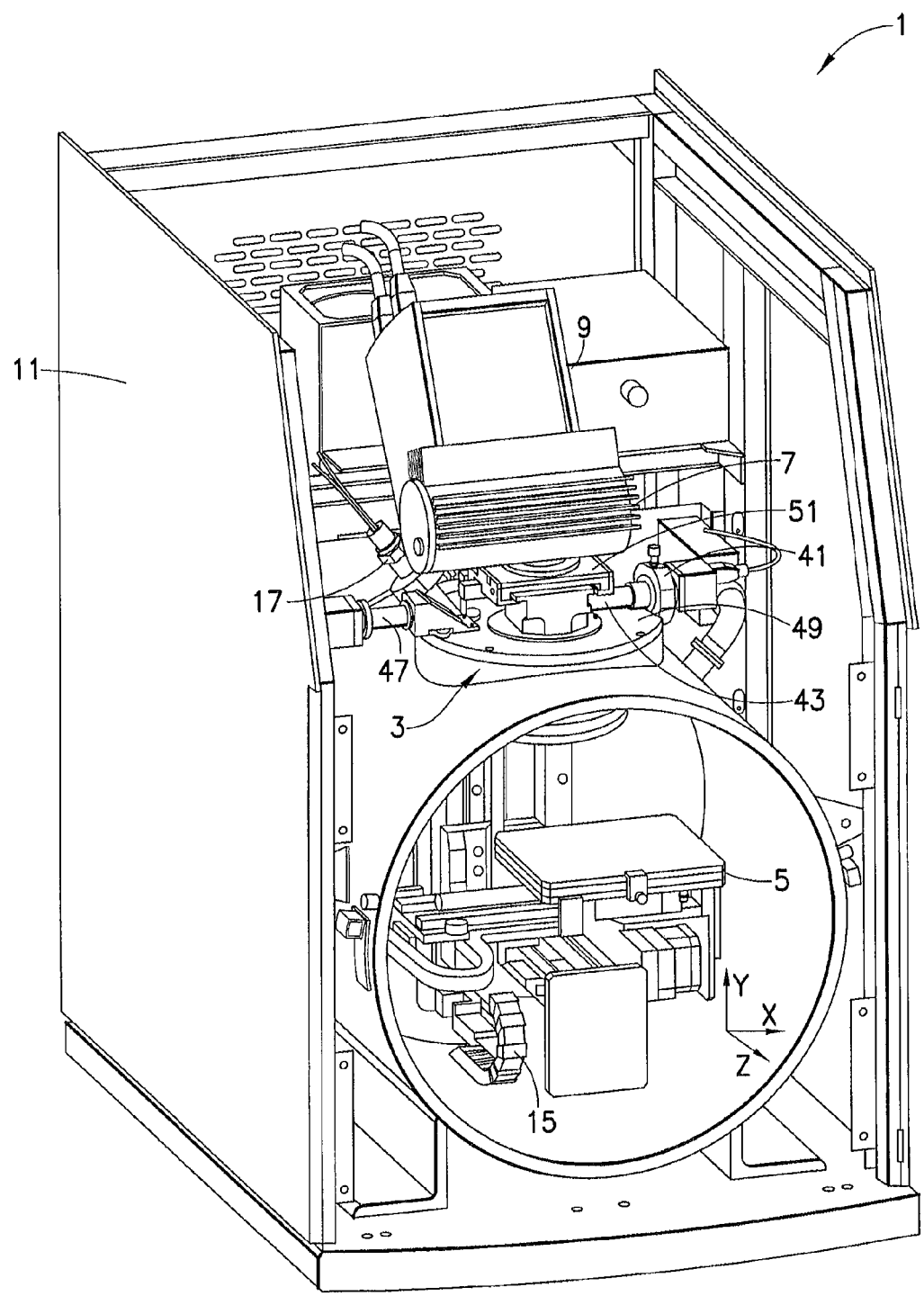
FIG. 2 is a front perspective view of the X-ray analyzer of FIG. 1 with a front face of the housing removed.
Figure 3:
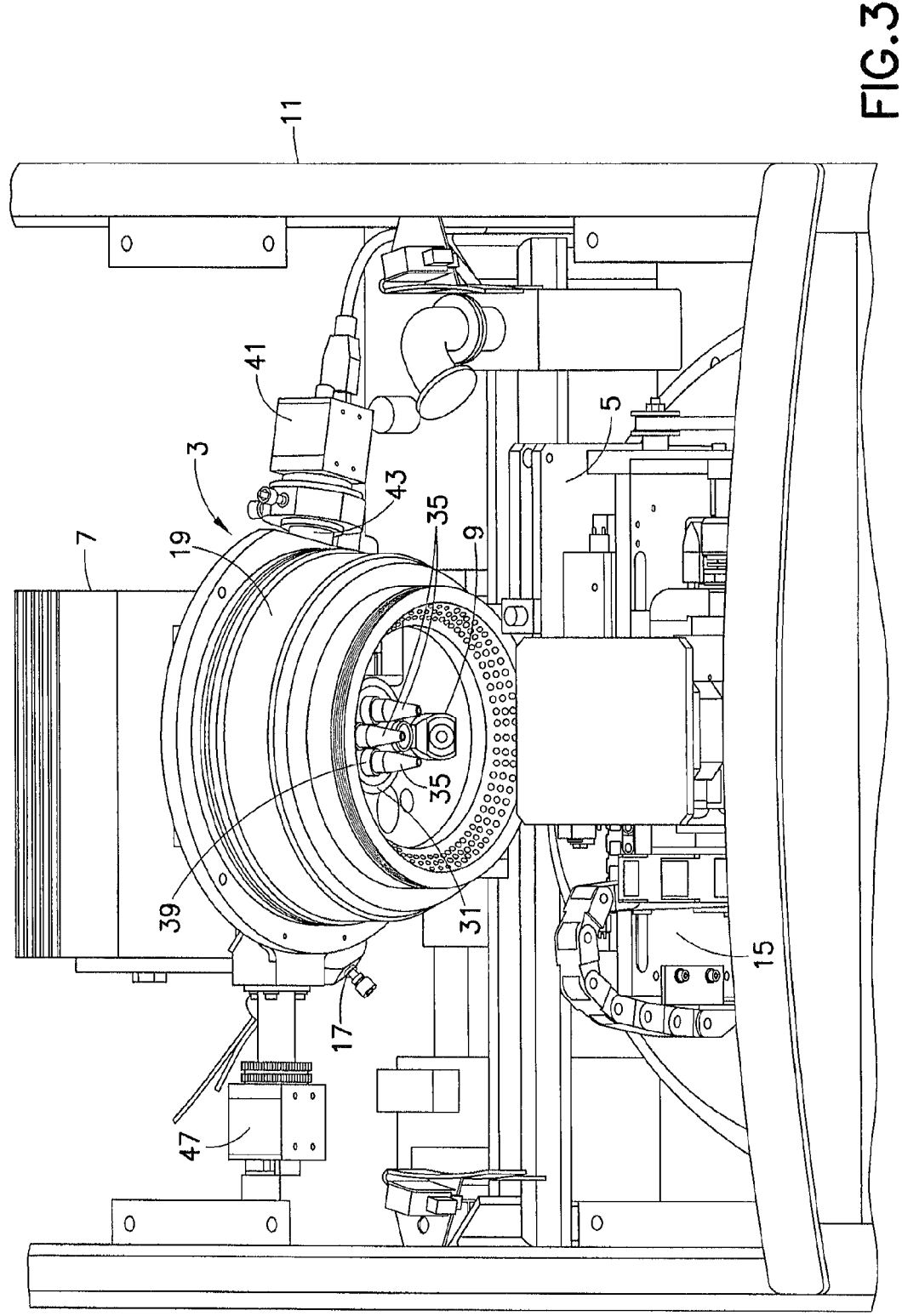
FIG. 3 is a partial bottom perspective view of the X-ray analyzer of FIG. 1 with the front face of the housing removed.

With reference to FIGS. 1-3, X-ray analyzer, denoted generally as reference numeral 1, includes an optical positioner assembly 3, a sample stage 5, an X-ray tube 7, and an X-ray detector 9. Each of these components is desirably positioned within an enclosure, such as housing 11. Housing 11 may include a door 13 on a front face thereof to allow an operator to mount a sample on sample stage 5 for analysis and to remove a sample after the analysis is completed.

Sample stage 5 is for holding and positioning a sample (not shown). Sample stage 5 is driven by a drive mechanism 15 to move in each of x, y, and z directions as shown by the coordinate axes in FIG. 2. The positioning of the sample is further aided through the use of at least one, and desirably two, lasers 17 as will be discussed hereinafter. The use of such a sample stage 5 as discussed hereinabove allows for multiple samples to be analyzed or for a single sample to be measured at different points.

Figure 4:
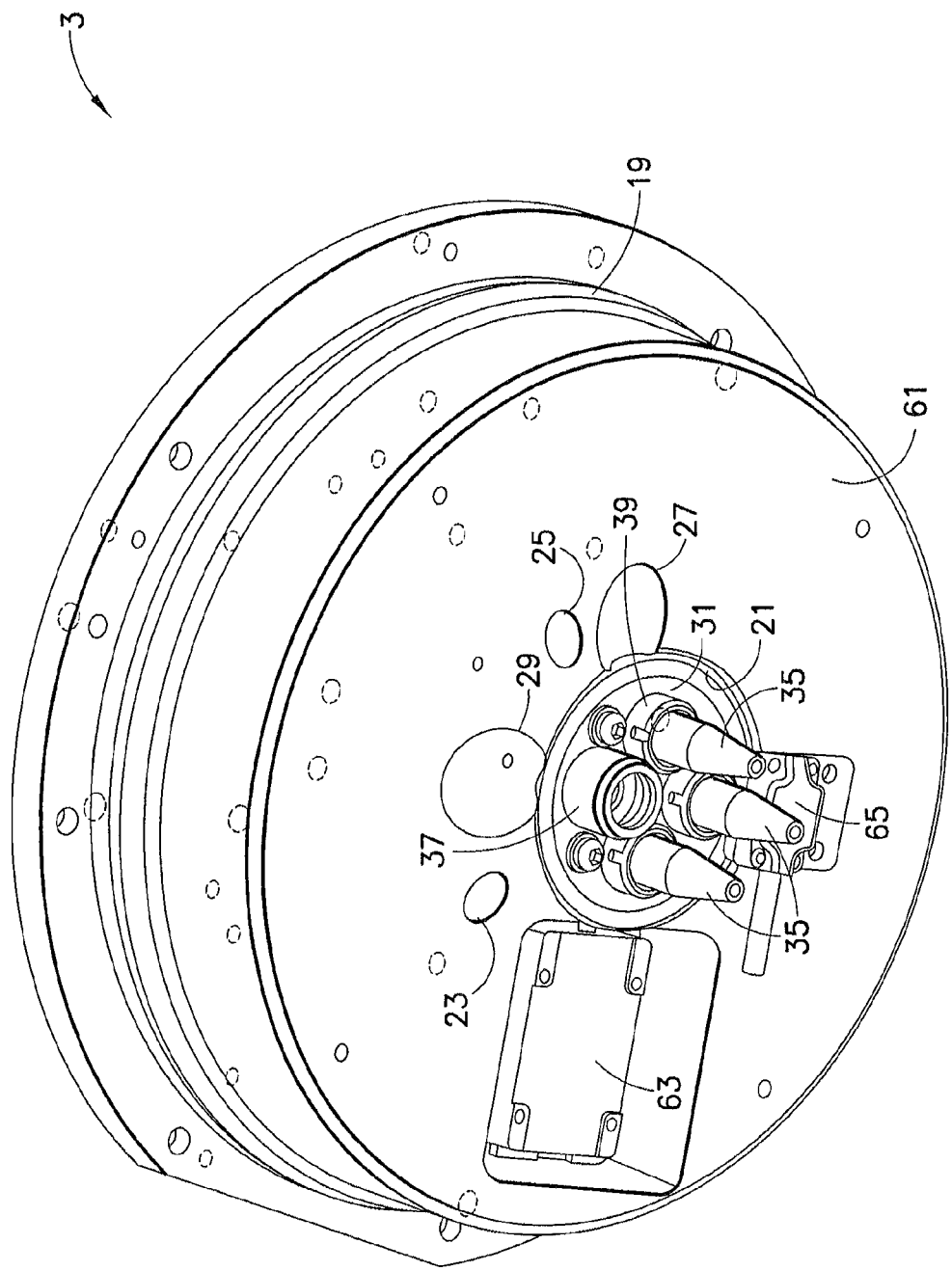
FIG. 4 is a bottom perspective view of a first embodiment of the optical positioner assembly of the X-ray analyzer of FIG. 1.

With reference to FIG. 4 and with continuing reference to FIGS. 1-3, optical positioner assembly 3 of X-ray analyzer 1 includes a body member 19 having an opening 21 and a plurality of ports 23, 25, 27, and 29. An optical positioner 31 is positioned within opening 21 of body member 19. As shown in FIG. 4, optical positioner 31 is embodied as a rotary turret. At least one, and desirably three (as shown) or more, X-ray optics 35 and an optical viewing lens 37 extend through ports provided in optical positioner 31 and are secured to optical positioner 31 with any suitable fastening mechanism, such as threaded sleeves 39. Optical viewing lens 37 is optically coupled to a high-resolution or high-magnification camera 41 by a lens assembly 43 such that camera 41 can produce optical images of the sample on sample stage 5 when positioned normal to sample stage 5. For exemplary purposes only, high-resolution camera 41 may be a Basler exA 1390-19m high resolution camera.

However, the arrangement illustrated in the various figures is not to be construed as limiting the present invention as it is possible to install more than three X-ray optics 35. The only limit is the physical size of optical positioner 31 and the physical size of X-ray optics 35. In addition, one or more of X-ray optics 35 may be replaced by another analytical beam path such as an Optical Spectrometer.

Each of X-ray optics 35 may produce a different spot size. The use of multiple X-ray optics 35 producing a variety of spot sizes allows for greater analytical flexibility. For instance, a small spot size allows for the analysis of a single particle or smaller area without including the surrounding material in the analysis. A larger spot size allows for an average result from many particles while making one measurement or it allows the user to map a larger area of a sample in a shorter time period. In addition, each of X-ray optics 35 is individually removable and can be replaced with a different X-ray optic 35 that produces a different spot size or replaced with another analytical beam path. This allows X-ray analyzer 1 of the present invention to be used for a variety of applications. X-ray optics 35 could also have different excitation characteristics or beam geometry (e.g., providing better excitation for a specific elemental X-ray line series like Cd(K)). X-ray optics 35 may be any combination of pin-hole collimaters, monocapillaries, polycapillaries, and monochromators in order to produce spectra optimized for the desired analysis, such as X-ray fluorescence, diffraction, Compton scattering, or transmission in radiography.

With reference to FIGS. 1-4, optical positioner assembly 3 further includes a low-resolution or low-magnification camera 47 extending through port 27 of body member 19 of optical positioner assembly 3. Low-resolution camera 47 is positioned such that it can obtain an image of the sample on sample stage 5. Low-resolution camera 47 can be used in conjunction with high-resolution camera 41 for a simultaneous view of the entire sample and a magnified view of an area of interest on the sample. For exemplary purposes only, low-resolution camera 47 may be a Basler exA 640-60c low-resolution camera. Alternatively, the system may be configured with "low-magnification" looking through optical positioner 31 and "high-magnification" looking through a port in body member 19.

Two lasers are provided with one of the lasers 17 extending through port 23 and the other laser extending through port 25 of body member 19. Lasers are provided to work in conjunction with sample stage 5 to properly position the sample. In addition, lasers 17 may be used to calibrate the position of sample stage 5 prior to using X-ray analyzer 1.

With continuing reference to FIGS. 1-4, the at least one X-ray tube 7 is configured to be fixedly mounted on a top surface 49 of body member 19 of optical positioner assembly 3. X-ray tube 7 is mounted on an X-ray mount 51 and is coupled to top surface 49 of body member 19 over opening 21 using bolts 53. X-ray mount 51 is sealed to opening 21 using, for example, an O-ring and a washer (not shown). X-ray tube 7 is mounted in such a manner that one of X-ray optics 35 positioned in optical positioner 31 aligns with an output of the at least one X-ray tube 7 such that the chosen X-ray optic 35 guides an X-ray beam generated by X-ray tube 7 to the sample on sample stage 5. More than one X-ray tube 7 may be used and each of the X-ray tubes 7 may be optimized for excitation conditions or for a particular type of X-ray analysis for example, elemental analysis by X-ray fluorescence spectroscopy, interatomic d-spacing analysis by X-ray diffraction, or atomic mass analysis by analysis of Compton scattering in the X-ray spectra.

The at least one X-ray detector 9 is configured to detect secondary X-rays from the sample on sample stage 5 when the sample is irradiated with a primary X-ray beam from X-ray tube 7. X-ray detector 9 includes a detecting element (not shown) for detecting the X-ray and an extension tube (not shown) for holding the detecting element. The extension tube is configured to pass through port 29 in body member 19 of optical positioner assembly 3 and is positioned off-axis from the X-ray spot produced by X-ray optics 35. The at least one X-ray detector may be an Energy Dispersive Detector such as a silicon (lithium drifted) detector, a silicon drift detector, a PIN detector, or a gas-filled proportional detector. More than one X-ray detector 9 may be provided such that each X-ray detector 9 is suitable for a particular spectral collection characteristic for example: energy resolved for X-ray fluorescence, intensity resolved for quantitative and Compton analysis, and directionally resolved for X-ray diffraction.

Figure 5:
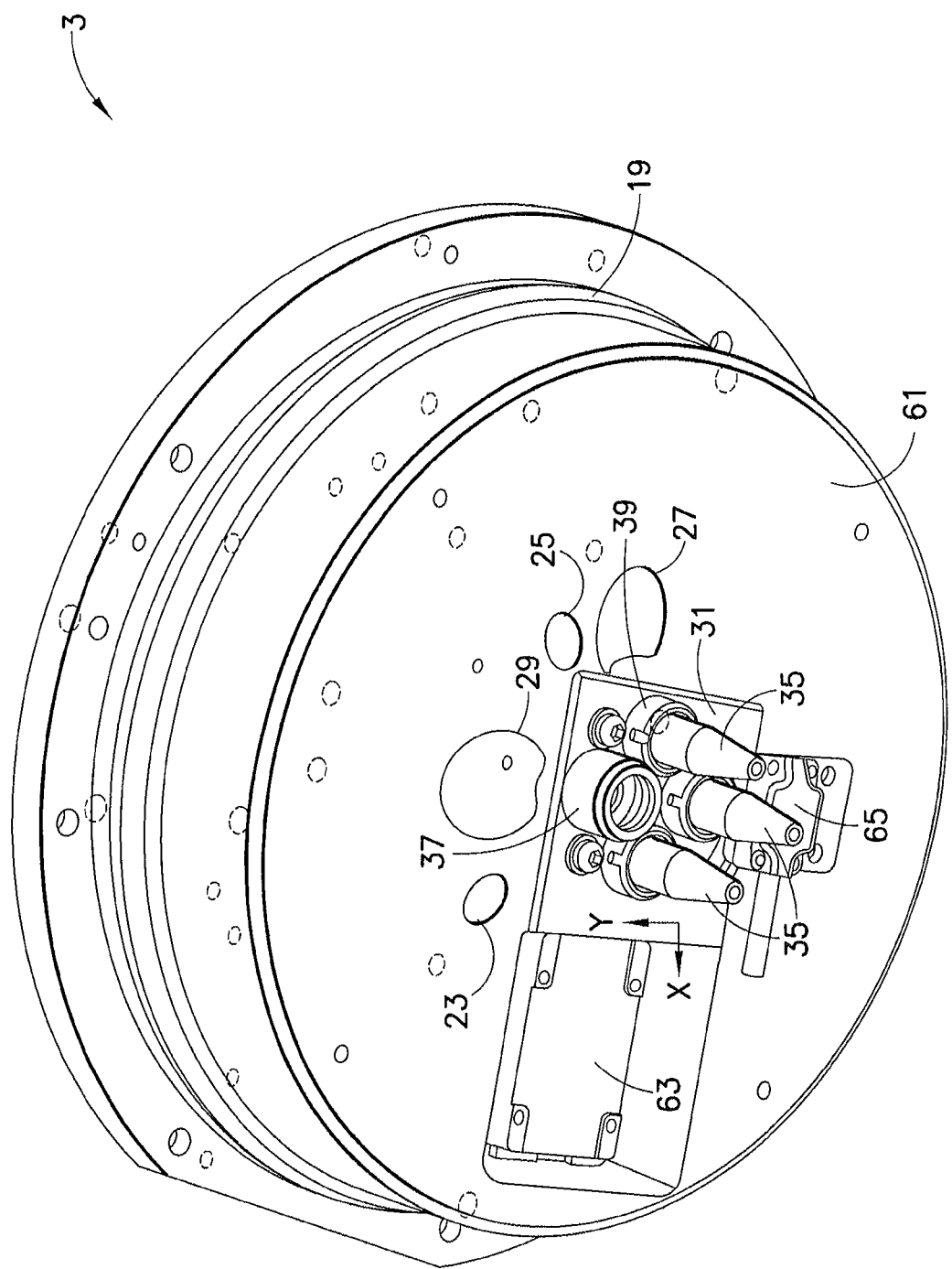
FIG. 5 is a bottom perspective view of an alternative embodiment of the optical positioner assembly of the X-ray analyzer of FIG. 1.

In operation, optical positioner 31 is configured to align within opening 21 of body member 19 to position optical viewing lens 37 or one of X-ray optics 35 normal to the sample on sample stage 5. In FIG. 4, optical positioner 31 is embodied as a rotary turret which rotates to align optical viewing lens 37 or the at least one X-ray optic 35 into position. In FIG. 5, optical positioner 31 is an x-y stage which translates to align optical viewing lens 37 or the at least one X-ray optic 35 into position.

Initially the sample is viewed through the optical viewing lens to a camera along a first path. Then, optical positioner 31 aligns one of X-ray optics 35 with the sample such that the X-ray optic 35 is positioned normal to the sample. When one of X-ray optics 35 is positioned normal to the sample, the sample is irradiated with primary X-rays along a second path. Accordingly, the sample will produce secondary X-ray spectra which are measured by the X-ray detector 9 along a third path. The output of X-ray detector 9 is X-ray spectra characteristic of the elemental, atomic mass, and interatomic d-spacing of the sample. Optimum excitation conditions for one or more of these X-ray analyses is achieved by selecting one or more specific X-ray optics 35 and excitation conditions of the X-ray tube 7.

Additionally, as mentioned hereinabove, an IR to UV optical spectrometer (not shown), such as a Raman spectrometer, may be positioned along a fourth path either through one or more of the ports of optical positioner 31 or through one or more of the ports 23, 25, 27, 29 of body member 19 to obtain molecular bond information of the sample. Optical positioner 31 can then align optical viewing lens 37 normal to the sample. In such a configuration, the optical viewing lens 37 receives light reflected from the sample along the first path thereby allowing high-resolution camera 41 to image the sample. The physical characteristics of a sample are determined from one or more of the X-ray or IR to UV spectral analyses.

Therefore, the X-ray analyzer of the present invention allows for coaxial analyzing and viewing of the sample because the first path and the second path, discussed hereinabove, are substantially coaxial. If an Optical Spectrometer is aligned with optics positioned in one of the ports of the optical positioner, then its analysis position is also coaxial.

Optical positioner 31 may be driven by a motive force provided by a piezoelectric motor 63 mounted on a bottom surface 61 of body member 19. However, the use of a piezoelectric motor is not to be construed as limiting the present invention as any other suitable type of motor may be utilized. Optical positioner 31 may include an optical encoder 65 to provide accuracy in positioning the at least one X-ray optics 35, the IR to UV optical spectrometer lens, such as a Raman spectrometer, and the optical viewing lens 37 normal to the sample on sample stage 5.

EXAMPLE

The following example is intended to be illustrative only and is not intended to limit the scope of the invention.

In order to perform analysis using X-ray analyzer 1 of the present invention, door 13 is opened and a sample or samples are mounted on sample stage 5. The ability of sample stage 5 to move allows for multiple samples to be analyzed or for a single sample to be measured at different points. Optical positioner 31 moves to align the optical viewing lens 37 to view and record images of the sample with the high-resolution camera 41. Sample stage 5 is moved to locate a point, points, or an area to be analyzed. Optical positioner 31 moves to align the X-ray optic 35 suitable for the type of analysis to be normal to the sample. Primary X-rays from X-ray tube 7 pass through the X-ray optic 35 and irradiate the spot on the sample coincident with the video image. X-ray detector 9 collects secondary X-ray spectra from the sample. Based on measurements of the secondary X-ray spectra obtained by X-ray detector 9, one or more additional X-ray optics 35 may be selected to optimize the measurement condition. Spectra from X-ray detector 9 may be analyzed for elemental information as determined from X-ray fluorescence data in the spectra, atomic spacing information as determined from diffraction data in the spectra, and atomic mass information as determined from Compton scatter in the spectra. The optical positioner ensures that the primary X-ray beam is coaxial with the video optics. If the Optical Spectrometer is aligned with optics positioned in one of the ports of optical positioner 31, then its analysis position is also coaxial. Molecular bonding information may be determined from optical spectra.

To create an analysis image, optical positioner 31 aligns optical viewing lens 37 to view the sample with high-resolution camera 41. Sample stage 5 is moved to locate an area to be analyzed. The area on the sample is specified as a matrix of analysis points using the video image obtained by the optical viewing lens 31 and camera 41. The appropriate X-ray optic 35 or an Optical Spectrometer optic is then positioned into place and the individual spectra at each analysis point are incorporated into a database correlated to pixels in the video image. Analysis images of elements, atomic spacing, atomic mass, or molecular bonding are created with pixel intensities calculated based on some property such as spectral line intensity or weight percentage. Each analysis point is related to a pixel in the video image.

Therefore, the X-ray analyzer of the present invention allows for coaxial analyzing and viewing of the sample because the first path and the second path, discussed hereinabove, are substantially coaxial. If the Optical Spectrometer is aligned with optics positioned in one of the ports of the optical positioner, then its analysis position is also coaxial.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements. Furthermore, it is to be understood that the present invention contemplates that, to the extent possible, one or more features of any embodiment can be combined with one or more features of any other embodiment.

The invention claimed is:

1. An X-ray analyzer comprising:
a sample stage for holding and positioning a sample;
an optical positioner assembly configured above the sample stage, the optical positioner assembly comprising:
a body member having an opening;
an optical positioner provided within the opening for aligning optical components within the opening;
at least one X-ray optic secured to the optical positioner; and
an optical viewing lens coupled to a first camera secured to the optical positioner;
at least one X-ray tube optically coupled to the at least one X-ray optic; and
at least one X-ray detector positioned to view the sample through a port of the body member of the optical positioner assembly,
wherein the optical positioner is configured to align one of the at least one X-ray optic and the optical viewing lens normal to the sample on the sample stage such that the sample is irradiated with X-rays along a first path when the X-ray optic is positioned normal to the sample and the optical viewing lens receives light reflected from the sample along a second path when the optical viewing lens is positioned normal to the sample.

2. The X-ray analyzer of claim 1, wherein the first path and the second path are substantially coaxial.

3. The X-ray analyzer of claim 1, wherein the optical positioner assembly includes a plurality of X-ray optics secured to the optical positioner.

4. The X-ray analyzer of claim 3, wherein each of the plurality of X-ray optics provides an X-ray beam to the sample having a different spot size.

5. The X-ray analyzer of claim 3, wherein the plurality of X-ray optics are pin-hole collimators, monocapillaries, polycapillaries, monochromators, or any combination thereof so as to produce spectra optimized for one of X-ray fluorescence, diffraction, Compton scattering, and transmission radiography.

6. The X-ray analyzer of claim 1, wherein the optical positioner assembly further includes at least one optic secured to the optical positioner for providing an optical path for an Optical Spectrometer.

7. The X-ray analyzer of claim 1, wherein the body member of the optical positioner assembly contains a plurality of ports with direct access paths to analysis points on the sample.

8. The X-ray analyzer of claim 7, wherein the at least one X-ray detector is positioned to view the sample through one of the plurality of ports provided in the body member of the optical positioner assembly, and wherein the X-ray detector is an Energy Dispersive Detector.

9. The X-ray analyzer of claim 7, wherein one of an Optical Spectrometer and an optical path for an Optical Spectrometer extend through one of the plurality of ports provided in the body member of the optical positioner assembly.

10. The X-ray analyzer of claim 7, further comprising a second camera positioned to view the sample through one of the plurality of ports provided in the body member of the optical positioner assembly.

11. The X-ray analyzer of claim 7, wherein the optical positioner assembly further comprises at least one laser extending through one of the plurality of ports of the body member for proper positioning of the sample stage.

12. The X-ray analyzer of claim 1, wherein the optical positioner is driven by a motive force.

13. The X-ray analyzer of claim 1, wherein an optical encoder is provided to interact with the optical positioner so as to provide accuracy in positioning one of the at least one X-ray optic and the optical viewing lens normal to the sample on the sample stage.

14. The X-ray analyzer of claim 1, wherein a second X-ray detector is positioned along the first path of the X-ray optic in such a way as to detect X-rays passing through the sample, and wherein the second X-ray detector is suitable for detecting high intensity X-rays.

15. The X-ray analyzer of claim 1, wherein the optical positioner is one of a rotary turret and an x-y stage.

16. An optical positioner assembly for use with an X-ray analyzer comprising:
a body member having an opening;
an optical positioner positioned within the opening;
at least one X-ray optic secured to the optical positioner; and
an optical viewing lens coupled to a first camera and secured to the optical positioner,
wherein the optical positioner is configured to align one of the at least one X-ray optic and the optical viewing lens normal to a sample.

17. The optical positioner assembly of claim 16, further comprising a plurality of X-ray optics secured to the optical positioner.

18. The optical positioner of claim 17, wherein each of the plurality of X-ray optics provides an X-ray beam from the an X-ray tube to the sample having a different spot size.

19. The optical positioner assembly of claim 17, wherein the plurality of X-ray optics are pin-hole collimators, monocapillaries, polycapillaries, monochromators, or any combination thereof so as to produce spectra optimized for one of X-ray fluorescence, diffraction, Compton scattering, and transmission radiography.

20. The optical positioner assembly of claim 16, further comprising at least one IR to UV optic, at least one optical spectrometer, or any combination thereof secured to the optical positioner so as to be positioned normal to the sample and mutually coaxial with the optical viewing lens.

21. The optical positioner assembly of claim 16, wherein the body member of the optical positioner assembly contains a plurality of ports with direct access paths to analysis points on the sample.

22. The optical positioner assembly of claim 21, wherein at least one X-ray detector is positioned to view the sample through one of the plurality of ports provided in the body member of the optical positioner assembly, and wherein the X-ray detector is an Energy Dispersive Detector.

23. The optical positioner assembly of claim 21, wherein one of an Optical Spectrometer and an optical path for an Optical Spectrometer extend through one of the plurality of ports provided in the body member of the optical positioner assembly.

24. The optical positioner assembly of claim 21, further comprising a second camera positioned to view the sample through one of the plurality of ports provided in the body member of the optical positioner assembly.

25. The optical positioner assembly of claim 21, wherein the optical positioner assembly further comprises at least one laser extending through at least one of the plurality of ports of the body member for proper positioning of a sample stage of the X-ray analyzer.

26. The optical positioner assembly of claim 16, wherein the optical positioner is driven by a motive force.

27. The optical positioner assembly of claim 16, wherein an optical encoder is provided to interact with the optical positioner so as to provide accuracy in positioning one of the at least one X-ray optic and the optical viewing lens normal to the sample on a sample stage.

28. The optical positioner assembly of claim 16, wherein the optical positioner is one of a rotary turret and an x-y stage.

29. A method of analyzing a sample comprising the steps of:
providing an X-ray analyzer comprising:
the sample stage for holding and positioning a sample;
an optical positioner assembly configured above the sample stage, the optical positioner assembly comprising:
a body member having an opening;
an optical positioner provided within the opening for aligning optical components within the opening;
at least one X-ray optic secured to the optical positioner; and
an optical viewing lens coupled to a camera and secured to the optical positioner;
at least one X-ray tube optically coupled to the at least one X-ray optic; and
at least one X-ray detector positioned to view the sample through a port of the body member of the optical positioner assembly;
placing the sample on the sample stage;
aligning the optical positioner until the optical viewing lens is positioned normal to the sample;
imaging a portion of the sample using the camera by receiving light reflected from the sample along a first path to obtain an image of the sample; and
locating a point, points, or areas for analysis.

30. The method of claim 29, further comprising the step of aligning the optical positioner until the at least one X-ray optic is positioned along a second path normal to the sample.

31. The method of claim 30, wherein the first path is substantially coaxial with the second path.

32. The method of claim 31, wherein elemental information is obtained from a secondary X-ray fluorescence spectra obtained by the X-ray detector.

33. The method of claim 31, wherein interatomic d-spacing information is obtained from a secondary X-ray diffraction spectra obtained by the X-ray detector.

34. The method of claim 31, wherein atomic mass information is obtained from a secondary X-ray Compton spectra obtained by the X-ray detector.

35. The method of claim 31, wherein X-ray absorption information is obtained from X-rays transmitted through the sample obtained by the X-ray detector.

36. The method of claim 31, wherein the optical positioner assembly further includes at least one optic secured to the optical positioner for providing an optical path for an Optical Spectrometer.

37. The method of claim 36, wherein molecular bonding information is obtained from an optical spectra obtained by the Optical Spectrometer.

38. The method of claim 31, further comprising the step of: correlating pixels of an image of the sample with one or more physical parameters of the sample.

39. The method of claim 38, wherein the one or more physical parameters are elemental composition, atomic spacing, atomic mass, X-ray absorption, molecular bonding, or any combination thereof.

* * * * *

UNITED STATES PATENT AND TRADEMARK OFFICE
CERTIFICATE OF CORRECTION

| | | |
|---|---|---|
| PATENT NO. | : 7,972,062 B2 | Page 1 of 1 |
| APPLICATION NO. | : 12/503878 | |
| DATED | : July 5, 2011 | |
| INVENTOR(S) | : Joseph A. Nicolosi | |

It is certified that error appears in the above-identified patent and that said Letters Patent is hereby corrected as shown below:

Column 10, Line 39, Claim 18, after "from" delete "the"

Signed and Sealed this
Eighteenth Day of October, 2011

David J. Kappos
*Director of the United States Patent and Trademark Office*